United States Patent [19]

Shon et al.

[11] Patent Number: 5,670,622
[45] Date of Patent: Sep. 23, 1997

[54] CONOTOXIN PEPTIDE PIIIA

[75] Inventors: Ki-Joon Shon; Doju Yoshikami; Maren Marsh; Lourdes J. Cruz; David R. Hillyard; Baldomero M. Olivera, all of Salt Lake City, Utah

[73] Assignee: University of Utah Research Foundation, Salt Lake City, Utah

[21] Appl. No.: 599,556

[22] Filed: Feb. 15, 1996

[51] Int. Cl.$^6$ .................................................. C07K 14/00
[52] U.S. Cl. ........................ 530/324; 530/325; 530/326; 530/855; 530/327
[58] Field of Search .................... 530/300, 324, 530/326, 325, 855

[56] References Cited

U.S. PATENT DOCUMENTS

| | | | |
|---|---|---|---|
| 4,447,356 | 5/1984 | Olivera et al. | 260/112.5 R |
| 5,051,403 | 9/1991 | Miljanich et al. | 514/12 |
| 5,189,020 | 2/1993 | Miljanich et al. | 514/12 |
| 5,264,371 | 11/1993 | Miljanich et al. | 436/503 |
| 5,424,218 | 6/1995 | Miljanich et al. | 436/503 |
| 5,432,155 | 7/1995 | Olivera et al. | 514/12 |
| 5,514,774 | 5/1996 | Olivera et al. | 530/324 |

FOREIGN PATENT DOCUMENTS

| | | | |
|---|---|---|---|
| WO 93/10145 | 5/1993 | WIPO | C07K 7/10 |
| WO 93/13128 | 7/1993 | WIPO | C07K 7/10 |
| WO 95/11256 | 4/1995 | WIPO | C07K 7/08 |

OTHER PUBLICATIONS

Colledge, C.J. et al. (1992). "Precursor Structure of ω–Conotoxin GVIA Determined from a cDNA Clone," *Toxicon* 30:1111–1116.

Cruz, L.J. and Olivera, B.M. (1986). "Calcium Channel Antagonists. ω–Conotoxin Defines a New High Affinity Site," *J. Biol. Chem.* 261:6230–6233.

Dudley, S.C. et al. (1995). "A μ–Conotoxin–Insensitive Na$^+$ Channel Mutant: Possible Localization of a Binding Site at the Outer Vestibule," *Biophysical J.* 69:1657–1665.

Fainzilber, M. et al. (1991). "Mollusc–specific toxins from the venom of *Conus textile neovicarius*," *Eur. J. Biochem.* 202:589–595.

Fainzilber, M. et al. (1994). "A New Neurotoxin Receptor Site on Sodium Channels Is Identified by a Conotoxin That Affects Sodium Channel Inactivation in Molluscs and Acts as an Antagonist in Rat Brain," *J. Biol. Chem.* 269:2574–2580.

Fainzilber, M. et al. (1994). "New Mollusc–Specific α–Conotoxins Block *Aplysia* Neuronal Acetylcholine Receptors," *Biochemistry* 33:9523–9529.

Gray, W.R. et al. (1981). "Peptide Toxins from *Conus geographus* Venom," *J. Biol. Chem.* 256:4734–4740.

Hasson, A. et al. (1993). "Alteration of Sodium Currents by New Peptide Toxins From the Venom of a Molluscivorous Conus Snail," *Eur. J. Neurosci.* 5:56–64.

Hillyard, D.R. et al. (1989). "A Molluscivorous Conus Toxin: Conserved Frameworks in Conotoxins," *Biochemistry* 28:358–361.

Hillyard, D.R. et al. (1992). "A New Conus Peptide Ligand for Mammalian Presynaptic Ca$^{2+}$ Channels," *Neuron* 9:69–77.

Hopkins, C. et al. (1995). "A New Family of Conus Peptides Targeted to the Nicotinic Acetylcholine Receptor," *J. Biol. Chem.* 270:22361–22367.

Kobayashi, J. et al. (1982). "Isolation of a Cardiotonic Glycoprotein, Striatoxin, from the Venom of the Marine Snail *Conus Striatus*," *Biochem. Biophys. Res. Comm.* 105:1389–1395.

Lundy, P.M. et al. (1991). "Pharmacological evidence for an ω–conotoxin, dihydropyridine–insensitive neuronal Ca$^{2+}$ channel," *Eur. J. Pharmacol.* 206:61–68.

McCleskey, E.W. et al. (1987). "ω–Conotoxin: Direct and persistent blockade of specific types of calcium channels in neurons but not muscle," *Proc. Natl. Acad. Sci. USA* 84:4327–4331.

McIntosh, M. et al. (1982). "Isolation and Structure of a Peptide Toxin from the Marine Snail *Conus magus*," *Arch. Biochem. Biophys.* 218:329–334.

McIntosh, J.M. et al. (1995). "A New Family of Conotoxins That Blocks Voltage–gated Sodium Channels," *J. Biol. Chem.* 270:16796–16802.

Monje, V.D. et al. (1993). "A New Conus Peptide Ligand For Ca Channel Subtypes," *Neuropharmacology* 32:1141–1149.

Myers, R.A. et al. (1993). "Conus Peptides as Chemical Probes for Receptors and Ion Channels," *Chem, Rev.* 93:1923–1936.

Olivera, B.M. et al. (1984). "Purification and Sequence of a Presynaptic Peptide Toxin from *Conus geographus* Venom," *Biochemistry* 23:5087–5090.

Olivera, B.M. et al. (1985). "Peptide Neurotoxins from Fish–Hunting Cone Snails," *Science* 230:1338–1343.

Olivera, B.M. et al. (1987). "Neuronal Calcium Channel Antagonists. Discrimination between Calcium Channel Subtypes Using ω–Conotoxin from *Conus magus* Venom," *Biochemistry* 26:2086–2090.

(List continued on next page.)

*Primary Examiner*—Donald E. Adams
*Assistant Examiner*—Jacqueline G. Krikorian
*Attorney, Agent, or Firm*—Venable, Baetjer, Howard & Civiletti, LLP

[57] ABSTRACT

The invention is directed to a new μ-conotoxin named GIIIA. μ-Conotoxin PIIIA consists of 22 amino residues and is found in the Eastern Pacific fish-hunting species *Conus purpurascens*. This conotoxin is a new Na$^+$ channel blocker and can be used to resolve tetrodotoxin-sensitive sodium channels into three categories: 1) sensitive to μ-PIIIA and μ-conotoxin GIIIA; 2) sensitive to μ-PIIIA but not to μ-GIIIA; and 3) sensitive to neither of these two μ-conotoxins. In rat brain, binding competition studies between the two μ-conotoxins and saxitoxin suggest at least three pharmacologically distinguishable binding sites. Thus, μ-conotoxin PIIIA should be a key tool for distinguishing among different sodium channel subtypes.

6 Claims, 5 Drawing Sheets

OTHER PUBLICATIONS

Olivera, B.M. et al. (1990). "Diversity of Conus Neuropeptides," *Science* 249:257–263.

Olivera, B.M. et al. (1991). "Conotoxins," *J. Biol. Chem.* 266:22067–22070.

Ramilo, C.A. et al. (1992). "Novel α–and ω–Conotoxins from Conus striatus Venom," *Biochemistry* 31:9919–9926.

Regan, L.J. et al. (1991). "Ca2+ Channels in Rat Central and Peripheral Neurons: High–Threshold Current Resistant to Dihydropyridine Blockers and ω–Conotoxin," *Neuron* 6:269–280.

Rivier, J. et al. (1987). "Neuronal Calcium Channel Inhibitors. Synthesis of ω–Conotoxin GVIA and Effects on $^{45}$Ca Uptake by Synaptosomes," *J. Biol. Chem.* 262:1194–1198.

Shon, K–J. et al. (1994). "δ–Conotoxin GmVIA, a Novel Peptide from the Venom of *Conus gloriamaris*," *Biochemistry* 33:11420–11425.

Shon, K–J. et al. (1995). "Purification, Characterization, Synthesis, and Cloning of the Lockjaw Peptide from *Conus purpurascens* Venom," *Biochemistry* 34:4913–4918.

Spira, M.E. et al. (1993). "Chemical and Electrophysiological Characterization of New Peptide Neurotoxins from the Venom of the Molluscivorous Snail *Conus textile neovicarius*: A Review," *Isr. J. Med. Sci.* 29:530–543.

Woodward, S.R. et al. (1990). "Constant and hypervariable regions in conotoxin propeptides," *EMBO J.* 9:1015–1020.

Yoshikami, D. et al. (1989). "The Inhibitory Effects of Omega–Conotoxins on Ca Channels and Synapses," *Ann. N.Y. Acad. Sci.* 560:230–248.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus purpurascens ( i x ) FEATURE:
        ( A ) NAME/KEY: Modified-site
        ( B ) LOCATION: 1
        ( D ) OTHER INFORMATION: /product="OTHER"
                / note="Amino acid 1 is pyroglutamate or glutamine."

( i x ) FEATURE:
        ( A ) NAME/KEY: Modified-site
        ( B ) LOCATION: 8
        ( D ) OTHER INFORMATION: /product="OTHER"
                / note="Amino acid 8 is 4-transhydroxyproline or
                proline."

( i x ) FEATURE:
        ( A ) NAME/KEY: Disulfide-bond
        ( B ) LOCATION: 4..16

( i x ) FEATURE:
        ( A ) NAME/KEY: Disulfide-bond
        ( B ) LOCATION: 5..21

( i x ) FEATURE:
        ( A ) NAME/KEY: Disulfide-bond
        ( B ) LOCATION: 11..22

( i x ) FEATURE:
        ( A ) NAME/KEY: Modified-site
        ( B ) LOCATION: 18
        ( D ) OTHER INFORMATION: /product="OTHER"
                / note="Amino acid 18 is 4-transhydroxyproline or
                proline."

( i x ) FEATURE:
        ( A ) NAME/KEY: Modified-site
        ( B ) LOCATION: 22
        ( D ) OTHER INFORMATION: /product="OTHER"
                / note="The carboxy terminus may be amidated."

( x i ) SEQUENCE DESCRIPTION: SEQ ID NO:1:

Xaa  Arg  Leu  Cys  Cys  Gly  Phe  Xaa  Lys  Ser  Cys  Arg  Ser  Arg  Gln  Cys
 1                    5                        10                       15

Lys  Xaa  His  Arg  Cys  Cys
              20

( 2 ) INFORMATION FOR SEQ ID NO:2:

( i ) SEQUENCE CHARACTERISTICS:
                ( A ) LENGTH: 4 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( v ) FRAGMENT TYPE: C-terminal ( v i ) ORIGINAL SOURCE:
                ( A ) ORGANISM: Conus purpurascens ( x i ) SEQUENCE DESCRIPTION: SEQ ID NO:2:

Cys  Cys  Gly  Arg
 1

( 2 ) INFORMATION FOR SEQ ID NO:3:

( i ) SEQUENCE CHARACTERISTICS:
                ( A ) LENGTH: 22 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Conus geographus ( i x ) FEATURE:
    ( A ) NAME/KEY: Modified-site
    ( B ) LOCATION: 6
    ( D ) OTHER INFORMATION: /product="4Hyp"
      / note="Amino acid 6 is 4-transhydroxyproline."

( i x ) FEATURE:
    ( A ) NAME/KEY: Modified-site
    ( B ) LOCATION: 7
    ( D ) OTHER INFORMATION: /product="4Hyp"
      / note="Amino acid 7 is 4-transhydroxyproline."

( i x ) FEATURE:
    ( A ) NAME/KEY: Modified-site
    ( B ) LOCATION: 17
    ( D ) OTHER INFORMATION: /product="4Hyp"
      / note="Amino acid 17 is 4-transhydroxyproline."

( i x ) FEATURE:
    ( A ) NAME/KEY: Disulfide-bond
    ( B ) LOCATION: 3..15

( i x ) FEATURE:
    ( A ) NAME/KEY: Disulfide-bond
    ( B ) LOCATION: 4..20

( i x ) FEATURE:
    ( A ) NAME/KEY: Disulfide-bond
    ( B ) LOCATION: 10..21

( i x ) FEATURE:
    ( A ) NAME/KEY: Modified-site
    ( B ) LOCATION: 22
    ( D ) OTHER INFORMATION: /product="OTHER"
      / note="The carboxy terminus is amidated."

( x i ) SEQUENCE DESCRIPTION: SEQ ID NO:3:

```
Arg Asp Cys Cys Thr Xaa Xaa Lys Lys Cys Lys Asp Arg Gln Cys Lys
 1               5                  10                  15
Xaa Gln Arg Cys Cys Ala
                20
```

( 2 ) INFORMATION FOR SEQ ID NO:4:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Conus geographus ( i x ) FEATURE:
    ( A ) NAME/KEY: Modified-site
    ( B ) LOCATION: 6
    ( D ) OTHER INFORMATION: /product="4Hyp"
      / note="Amino acid 6 is 4-transhydroxyproline."

( i x ) FEATURE:
    ( A ) NAME/KEY: Modified-site
    ( B ) LOCATION: 7
    ( D ) OTHER INFORMATION: /product="4Hyp"
      / note="Amino acid 7 is 4-transhydroxyproline."

( i x ) FEATURE:
      ( A ) NAME/KEY: Modified-site
      ( B ) LOCATION: 17
      ( D ) OTHER INFORMATION: /product="4Hyp"
          / note="Amino acid 17 is 4-transhydroxyproline."

( i x ) FEATURE:
      ( A ) NAME/KEY: Disulfide-bond
      ( B ) LOCATION: 3..15

( i x ) FEATURE:
      ( A ) NAME/KEY: Disulfide-bond
      ( B ) LOCATION: 4..20

( i x ) FEATURE:
      ( A ) NAME/KEY: Disulfide-bond
      ( B ) LOCATION: 10..21

( i x ) FEATURE:
      ( A ) NAME/KEY: Modified-site
      ( B ) LOCATION: 22
      ( D ) OTHER INFORMATION: /product="OTHER"
          / note="The carboxy terminus is amidated."

( x i ) SEQUENCE DESCRIPTION: SEQ ID NO:4:

```
Arg  Asp  Cys  Cys  Thr  Xaa  Xaa  Arg  Lys  Cys  Lys  Asp  Arg  Arg  Cys  Lys
1                    5                          10                          15
Xaa  Met  Lys  Cys  Cys  Ala
                20
```

( 2 ) INFORMATION FOR SEQ ID NO:5:

( i ) SEQUENCE CHARACTERISTICS:
      ( A ) LENGTH: 22 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v i ) ORIGINAL SOURCE:
      ( A ) ORGANISM: Conus geographus ( i x ) FEATURE:
      ( A ) NAME/KEY: Modified-site
      ( B ) LOCATION: 6
      ( D ) OTHER INFORMATION: /product="4Hyp"
          / note="Amino acid 6 is 4-transhydroxyproline."

( i x ) FEATURE:
      ( A ) NAME/KEY: Modified-site
      ( B ) LOCATION: 7
      ( D ) OTHER INFORMATION: /product="OTHER"
          / note="Amino acid 7 is 4-transhydroxyproline."

( i x ) FEATURE:
      ( A ) NAME/KEY: Modified-site
      ( B ) LOCATION: 17
      ( D ) OTHER INFORMATION: /product="4Hyp"
          / note="Amino acid 17 is 4-transhydroxyproline."

( i x ) FEATURE:
      ( A ) NAME/KEY: Disulfide-bond
      ( B ) LOCATION: 3..15

( i x ) FEATURE:
      ( A ) NAME/KEY: Disulfide-bond
      ( B ) LOCATION: 4..20

( i x ) FEATURE:
      ( A ) NAME/KEY: Disulfide-bond
      ( B ) LOCATION: 10..21

( i x ) FEATURE:
      ( A ) NAME/KEY: Modified-site (B) LOCATION: 22
        (D) OTHER INFORMATION: /product="OTHER"
            /note="The carboxy terminus is amidated."

(xi) SEQUENCE DESCRIPTION: SEQ ID NO:5:

Arg  Asp  Cys  Cys  Thr  Xaa  Xaa  Lys  Lys  Cys  Lys  Asp  Arg  Arg  Cys  Lys
1                   5                        10                       15

Xaa  Leu  Lys  Cys  Cys  Ala
                20

(2) INFORMATION FOR SEQ ID NO:6:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Conus purpurascens (ix) FEATURE:
        (A) NAME/KEY: CDS
        (B) LOCATION: 1..81

(xi) SEQUENCE DESCRIPTION: SEQ ID NO:6:

GAA  AAG  AGA  CAA  CGA  CTG  TGT  TGC  GGT  TTT  CCG  AAG  AGT  TGC  AGA  TCC        48
Glu  Lys  Arg  Gln  Arg  Leu  Cys  Cys  Gly  Phe  Pro  Lys  Ser  Cys  Arg  Ser
1                   5                        10                       15

CGA  CAA  TGC  AAA  CCT  CAT  AGG  TGT  TGC  GGA  CGA  TAA                            84
Arg  Gln  Cys  Lys  Pro  His  Arg  Cys  Cys  Gly  Arg
                20                        25

(2) INFORMATION FOR SEQ ID NO:7:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:7:

Glu  Lys  Arg  Gln  Arg  Leu  Cys  Cys  Gly  Phe  Pro  Lys  Ser  Cys  Arg  Ser
1                   5                        10                       15

Arg  Gln  Cys  Lys  Pro  His  Arg  Cys  Cys  Gly  Arg
                20                        25

CONOTOXIN PEPTIDE PIIIA

This ivention was made with Government support under Grant No. P01 GM 48677 awarded by the National Institutes of Health, Bethesda, Md. The United States Government has certain rights in the invention.

BACKGROUND OF THE INVENTION

This invention relates to relatively short peptides about 22 residues in length, which are naturally available in minute amounts in the venom of the cone snails or analogous to the naturally available peptides, and which include three cyclizing disulfide linkages.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Mollusks of the genus Conus produce a highly toxic venom which enables them to carry out their unique predatory lifestyle. Prey are immobilized by the venom which is injected by means of a highly specialized venom apparatus, a disposable hollow tooth which functions both in the manner of a harpoon and a hypodermic needle.

Few interactions between organisms are more striking than those between a venomous animal and its envenomated victim. Venom may be used as a primary weapon to capture prey or as a defense mechanism. These venoms disrupt essential organ systems in the envenomated animal, and many of these venoms contain molecules directed to receptors and ion channels of neuromuscular systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid- encoded translation products having defined conformations, and as such, they are somewhat unusual. Peptides in this size range normally equilibrate among many conformations. Proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used; however, every Conus species uses fundamentally the same basic pattern of envenomation.

The major paralytic peptides in these fish-hunting cone venoms were the first to be identified and characterized. In C. geographus venom, three classes of disulfide-rich peptides were found: the α-conotoxin peptides (which target and block the nicotinic acetylcholine receptors); the μ-conotoxin peptides (which target and block the skeletal muscle $Na^+$ channels); and the ω-conotoxin peptides (which target and block the presynaptic neuronal $Ca^{2+}$ channels). However, there are multiple homologs in each toxin class; for example, there are at least five different ω-conotoxin peptides present in C. geographus venom alone. Considerable variation in sequence is evident, and when different ω-conotoxin peptide sequences were first compared, only the cysteine residues that are involved in disulfide bonding and one glycine residue were found to be invariant. Another class of conotoxins found in C. geographus venom is that referred to as conantokins, which cause sleep in young mice and hyperactivity in older mice and are targeted to the NMDA receptor. Each cone venom appears to have its own distinctive group, or signature, of different conotoxin sequences.

Many of these peptides have now become fairly standard research tools in neuroscience and can be used as chemical probes for receptors and ion channels (Myers et at., 1993). μ-Conotoxin peptides, because of their ability to preferentially block muscle but not axonal $Na^+$ channels, are convenient tools for immobilizing skeletal muscle without affecting axonal or synaptic events. ω-Conotoxin peptides have become standard pharmacological reagents for investigating voltage-sensitive $Ca^{2+}$ channels and are used to block presynaptic termini and neurotransmitter release. Several conotoxin peptides have also found utility in screening newly isolated conotoxin peptides or analogs for medical purposes (Miljardch et at., 1993).

Many potent toxins target voltage-gated sodium channels; these have been indispensable for investigating the structure and function of these ion channels which play a key role in excitable tissues. The demonstration that tetrodotoxin specifically inhibited voltage-gated sodium currents without effect on potassium currents provided crucial experimental support for the Hodgkin-Huxley formulation of action potential generation (Narahashi et at., 1964). A variety of ligands for the $Na^+$ channel has been discovered since, and their sites of binding and modes of activity have been investigated (Catterall, 1992).

Site I is the classical binding site for channel blockers, notably the guanidinium toxins, saxitoxin (STX) and tetrodotoxin (TTX); this site is generally postulated to be at the extracellular end of the channel pore. Only one family of polypeptide toxins, the μ-conotoxins, has been shown to act at this site and functionally affect voltage-gated sodium currents. These were originally isolated from the venom of the marine snail Conus geographus (Stone et at., 1982; Sato et at., 1983; Cruz et at., 1985; and Olivera et at., 1985).

Other families of Conus peptides (notably the ω-conotoxins which target calcium channels and the α-conotoxins which target nicotinic acetylcholine receptors) have been found in the venoms of many Conus species examined. They show extreme variability among homologous peptides from different Conus species, and interspecific comparison of different members within a given family of Conus peptides has provided insightful structure-function information. In particular, the wide diversity among natural toxins in these families has been instrumental in identifying new classes of receptors (Olivera et at., 1990; Olivera et at., 1994). By contrast, because the μ-conotoxins have so far been described only from the venom of C. geographus, most structure-function information for this peptide family has come from experiments with synthetic analogs.

The present invention describes a new member of the μ-conotoxin peptide family - μ-conotoxin PIIIA from Conus purpurascens, an Eastern Pacific fish-hunting species. As expected, the new μ-conotoxin shows considerable sequence divergence from the μ-conotoxins of Conus geographus. In addition to a comprehensive biochemical characterization of the peptide, there is provided electrophysiological and binding data which demonstrate that μ-conotoxin PIIIA is a powerful pharmacological tool for distinguishing among different tetrodotoxin-sensitive $Na^+$ channel subtypes. The tetrodotoxin-sensitive sodium channels can now be resolved into three categories: 1) sensitive to μ-PIIIA and μ-conotoxin GIIIA; 2) sensitive to μ-PIIIA but not to μ-GIIIA; and 3) sensitive to neither μ-conotoxin (examples are skeletal muscle, rat brain Type II and motor axon subtypes, respectively). In rat brain, binding competition studies between the two μ-conotoxins and [$^3$H] saxitoxin suggest at least three pharmacologically distinguishable binding sites.

Thus, μ-conotoxin PIIIA is a key tool for distinguishing among different sodium channel subtypes.

SUMMARY OF THE INVENTION

The present invention is directed to conotoxin peptides having 22 amino acids, six cysteines which form three disulfide bonds between the first and fourth, second and fifth, and third and sixth cysteines, respectively. The invention is directed to μ-conotoxin PIIIA having the formula Xaa$_1$-Arg-Leu-Cys-Cys-Gly-Phe-Xaa$_2$-Lys-Ser-Cys-Arg-Ser-Arg-Gln-Cys-Lys-Xaa$_2$-His-Arg-Cys-Cys (SEQ ID NO:1) where Xaa$_1$ represents pyroglutamate or glutamine and Xaa$_2$ represents 4-trans-hydroxyproline or proline. This peptide targets sodium channels.

BRIEF DESCRIPTION OF THE FIGURES

FIG. 4A shows whole cell current recorded from an oocyte expressing rat type II Na$^+$ channels. Voltage steps ranging from −80 mV to +60 mV, in 10 mV increments, were generated from a holding potential of −100 mV. FIG. 4B shows results (profound block of the currents) when 2 mM PIIIA was added to the bath solution. FIG. 4C shows the results following a wash with Normal Frog Ringers solution.

DETAILED DESCRIPTION OF THE PREFERRED EMBODIMENT

Figure 1A:
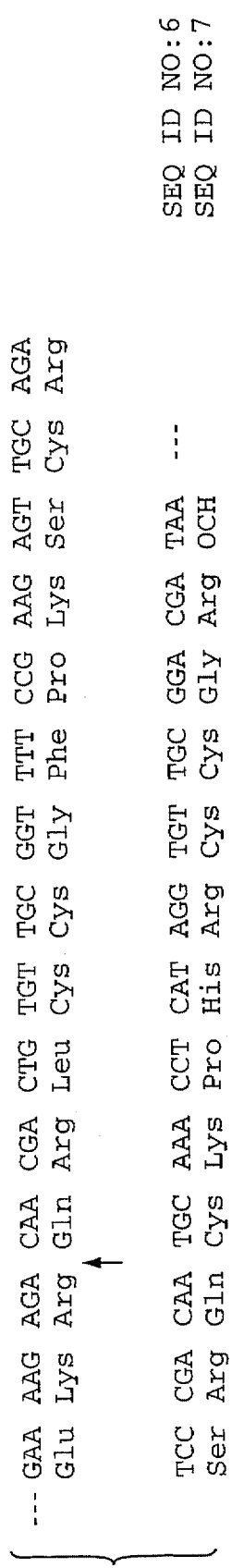
FIG. 1A shows the nucleic acid sequence derived by analyzing cDNA clones from a *Conus purpurascens* venom duct library. The sequence encoding the inferred C-terminal end of the open reading frame is shown; mature conotoxins are always encoded at the C-terminus of the precursor sequence. The pattern of Cys residues suggested that the encoded C-terminal peptide might be a μ-conotoxin. The arrow indicates the predicted site of proteolytic cleavage to generate the mature toxin. A-Lys-Arg- sequence is the most common motif for proteolytic cleavage of conotoxin precursors.

The present invention is directed to conotoxin peptides having 22 amino acids, six cysteines which form three disulfide bonds between the first and fourth, second and fifth, and third and sixth cysteines, respectively, and to the precursors of these peptides. The invention is directed to μ-conotoxin PIIIA having the formula Xaa$_1$-Arg-Leu-Cys-Cys-Gly-Phe-Xaa$_2$-Lys-Ser-Cys-Arg-Ser-Arg-Gln-Cys-Lys-Xaa$_2$-His-Arg-Cys-Cys(SEQ ID NO: 1) where Xaa$_1$ represents pyroglutamate or glutamine and Xaa$_2$ represents 4-trans-hydroxyproline or proline and is also directed to precursors of these peptides and nucleic acids encoding these peptides. This peptide is a sodium channel blocker and is useful as an active agent for muscle contraction in instances where lack of muscle contraction is problematic, such as for treating urinary or fecal incontinence. It is also useful as an active agent for anti-seizures, e.g., an anti-epileptic. Further, this conotoxin may also be useful for tagging tumors since they are able, as are other conotoxins, to detect antibodies which form against tumors. Since conotoxins bind to cell surface receptors, ion channels, they are capable of inhibiting tumor growth and are useful as antineoplastic agents.

Chemical Synthesis of Conotoxins

These peptides are sufficiently small to be chemically synthesized. General chemical syntheses for preparing the foregoing conotoxin peptides are described hereinafter, along with specific chemical syntheses of several conotoxin peptides and indications of biological activities of these synthetic products. Various ones of these conotoxin peptides can also be obtained by isolation and purification from specific Conus species using the technique described in U.S. Pat. No. 4,447,356 (Olivera et at., 1984), the disclosure of which is incorporated herein by reference.

Although the conotoxin peptides of the present invention can be obtained by purification from cone snails, because the amounts of conotoxin peptides obtainable from individual snails are very small, the desired substantially pure conotoxin peptides are best practically obtained in commercially valuable amounts by chemical synthesis. For example, the yield from a single cone snail may be about 10 micrograms or less of conotoxin peptide. By "substantially pure" is meant that the peptide is present in the substantial absence of other biological molecules of the same type; it is preferably present in an amount of at least about 85% by weight and preferably at least about 95% of such biological molecules of the same type which are present (i.e., water, buffers and innocuous small molecules may be present). Chemical synthesis of biologically active conotoxin peptides depends of course upon correct determination of the amino acid sequence.

The conotoxin peptides can also be produced by recombinant DNA techniques well known in the art. Such techniques are described by Sambrook et al. (1979). The peptides produced in this manner are isolated, reduced if necessary, and oxidized to form the correct disulfide bonds.

One method of forming disulfide bonds in the conotoxin peptides of the present invention is the air oxidation of the linear peptides for prolonged periods under cold room temperatures. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conotoxin molecule. However, because of the dilution resulting from the presence of other fractions of less biopotency, a somewhat higher dosage may be required.

A second method of forming the disulfide bonds in the conotoxin peptides of the present invention involves the use of acetamidomethyl (Acm) as protection agent on the second and fifth cysteines during the synthesis of the conotoxin peptides. The use of Acm on these two residues is based on the analogy with disulfide bridges in other conotoxin peptides. The peptide with the Acm protected cysteines is air-oxidized overnight at room temperature. The bicyclic peptides are separated by high performance liquid chromatography (HPLC) and the desired isomer isolated. The final disulfide bridge is carried out by iodination. The undesired isomers are efficiently recycled by reduction to linear peptide. The desired isomer is determined by a partial reduction analysis (Gray, 1993). In this analysis, a sample of a bicyclic precursor is treated with tris-[2-carboxyethyl]-phosphine to give linear peptide and a singly-bridged intermediate. The latter peptide is reacted with iodoacetamide, and the location of alkylated cysteine residues is established by sequence analysis. In this analysis, it was determined that the correct linkages were between the first and fourth, second and fifth, and third and sixth cysteines for GmVIA, for example.

The peptides are synthesized by a suitable method, such as by exclusively solid-phase techniques, by partial solid-phase techniques, by fragment condensation or by classical solution couplings. The employment of recently developed recombinant DNA techniques may be used to prepare these peptides, particularly the longer ones containing only natural amino acid residues which do not require post-translational processing steps.

In conventional solution phase peptide synthesis, the peptide chain can be prepared by a series of coupling reactions in which the constituent amino acids are added to the growing peptide chain in the desired sequence. The use of various N-protecting groups, e.g., dicyclohexylcarbodiimide or carbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et at., 1978). The fragment condensation method of synthesis is exemplified in U.S. Pat. No. 3,972,859 (1976). Other available syntheses are exemplified by U.S. Pat. Nos. 3,842,067 (1974) and 3,862,925 (1975).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chin protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et at., (1966). Chloromethylated resins are commercially available from Bio Rad Laboratories (Richmond, CA) and from Lab. Systems, Inc. The preparation of such a resin is described by Stewart et al. (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH BHA resin support, or —NH—MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Komreich et at., 1986) can be used, or should still other groups than the free acid be desired at the C-terminus, it may be preferable to synthesize the peptide using classical methods as set forth in the Houben-Weyl text (1974).

The C-terminal amino acid, protected by Boc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$(1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et at. (1970). Coupling reactions can be performed automatically, as on a Beckman 990 automatic synthesizer, using a program such as that reported in Rivier et at. (1978).

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptidoresin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF), followed by oxidation as described above.

Comparison of Conotoxin Classes

The present studies establish that *Conus purpurascens* venom ducts express a μ-conotoxin which has clear homology to the three previously characterized μ-conotoxins from *Conus geographus* venom. The peptide from *Conus purpurascens*, μ-conotoxin GIIIA, like the μ-conotoxins from *Conus geographus* (Table I) is highly positively charged and has the same disulfide framework. However, of the sixteen non-cysteine amino acids in μ-conotoxin GIIIA, only five are identical in all four peptides (Arg2, Hyp8, Arg14, Lys17 and Hyp18). Some of the most strikingly divergent substitutions (Leu3 for Asp, Phe7 for Hyp) involve replacement of a hydrophilic by a hydrophobic amino acid, making μ-PIIIA significantly more hydrophobic. The conservation of Arg14, indicated by the arrow in Table I would have been predicted from structure/function studies carried out on μ-conotoxin GIIIA, which suggested that this residue was critical for biological activity. A detailed hypothesis for the placement of this residue within the vestibule of the sodium channel has been offered (Dudley et at., 1995).

Potentially, the most useful result of the present study is the difference in $Na^+$ channel subtype specificity of μ-conotoxin PIIIA vs. GIIIA. μ-Conotoxin PIIIA appears to target a wider spectrum of mammalian voltage-gated sodium channel subtypes than does μ-GIIIA. μ-Conotoxin PIIIA was able to displace a larger fraction of specific [$^3$H]STX binding to high affinity rat brain sites than could μ-GIIIA. However, not all [$^3$H]STX binding sites could be displaced by μ-PIIIA even at high peptide concentrations, suggesting that μ-PIIIA could discriminate between different classes of [$^3$H]STX binding sites in the mammalian central nervous system.

Figure 4A:
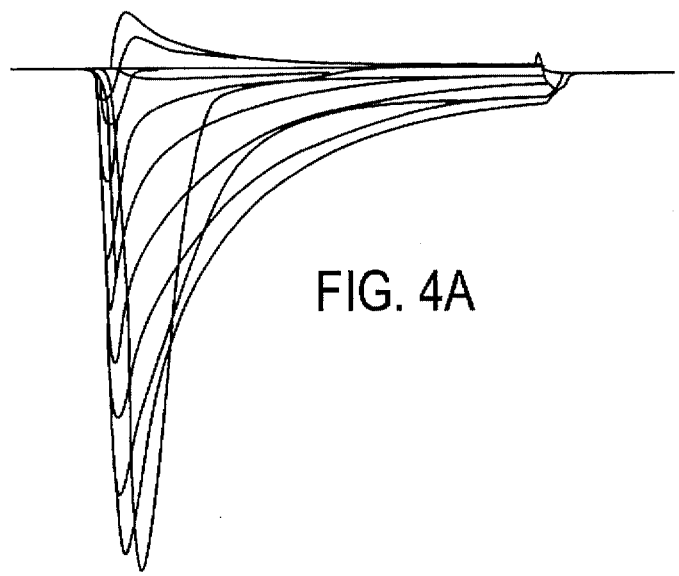
FIGS. 4A, 4B and 4C show that μ-PIIIA blocks rat type II Na$^+$ channel expressed in Xenopus oocytes.
Figure 4B:

At the present time, voltage-gated sodium channels are primarily distinguished in situ by their tetrodotoxin sensitivity or insensitivity. The discovery and characterization of μ-conotoxin PIIIA described above provides the basis for dividing tetrodotoxin-sensitive sodium channels into three categories distinguishable by their sensitivity to μ-conotoxins:

1) Voltage-gated sodium channels which are sensitive to both μ-PIIIA and μ-GIIIA. An example of this subtype is the skeletal muscle subtype in both frog and mammalian systems. The binding data in FIG. 4 are suggestive that there are central nervous system sodium channels that also fit into this category, but that they would represent only a minor fraction of the total STX/TTX-sensitive voltage-gated sodium channels present in adult rat brain.

2) A class of voltage-gated sodium channels that are sensitive to both TTX and μ-GIIIA, but which are significantly more resistant to μ-GIIIA. FIG. 4 shows that rat brain Type II sodium channels belong to this category; the Type II channels may account for the binding data in FIG. 3 which demonstrate that a significant fraction of the total [3H]STX high affinity sites in the central nervous system are displaced by μ-PIIIA but not by μ-GIIIA.

3) Finally, both the binding data and the electrophysiology strongly suggest that a significant fraction oftetrodotoxin-sensitive sodium channels will be resistant to both μ-PIIIA and μ-GIIIA. An example of this category would be the voltage-gated sodium channels present in motor axons, which are resistant to both μ-conotoxins. The binding data indicate that a major fraction of the total CNS channels may fall into this category. In addition, the results indicate that the subtype of voltage-gated sodium channels present in motor axons must be distinct from the Type II sodium channels present in the mammalian central nervous system.

The discovery of μ-conotoxin PIIIA is also indicative that the μ-conotoxin peptide family may be broadly distributed in Conus species. Different μ-conotoxin sequence variants found in the about 500 species of Conus may be expected to exhibit different affinities for the various voltage-gated sodium channel subtypes. The situation is somewhat analogous to that found for the ω-conotoxins, where the subtype specificity of different ω-conotoxin peptides has been used to advantage to investigate the functional roles of different $Ca^{2+}$ channel subtypes. Similarly, the μ-conotoxins should prove useful for dissecting the role of an individual $Na^+$ channel subtype in a neuron, circuit or event slice preparation, particularly in those situations when multiple molecular forms of voltage-gated $Na^+$ channels are present.

EXAMPLES

The present invention is described by reference to the following Examples, which are offered by way of illustration and are not intended to limit the invention in any manner. Standard techniques well known in the art or the techniques specifically described below were utilized.

Figure 1B:
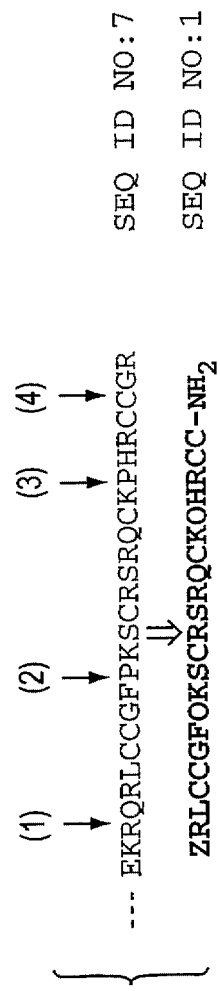
FIG. 1B shows the predicted sequence of the post-translationally processed peptide. The amino acid sequence shown in FIG. 1A would be predicted to be post-translationally processed at the four indicated sites as follows: proline would be hydroxylated to 4-trans-hydroxyproline (sites 2 and 3); the C-terminal -Cys-Gly-Arg- sequence would be processed by an exopeptidase and amidation enzymes to a -Cys-NH$_2$ moiety (site 4); and after proteolysis the encoded glutamine residue would be converted to pyroglutamate (site 1). The post-translational processing events would yield the indicated bold sequence (Z=pyroglutamate, O=4 trans-hydroxyproline).

Example 1 Identification of a cDNA Clone from *Conus purpurascens* Encoding a Putative μ-Conotoxin The feasibility of discovering new Conus peptides from the predicted amino acid sequences encoded by cDNA clones was previously demonstrated with ω-conotoxins (Hillyard et at., 1992). The method involves preparing cDNA libraries and screening these with mixed oligonucleotides in a manner similar to that described by Hillyard et at. (1992). A cDNA library was prepared using mRNA from the venom duct of *C. purpurascens* as previously described (Woodward et at., 1990; Colledge et at., 1992) and this library was subsequently screened using mixed oligonucleotides to identify clones putatively encoding conotoxins. Many positive clones were identified and sequenced. Several of these cDNA clones contained the nucleotide sequence shown in FIG. 1. The predicted amino acid sequence form this nucleotide sequence strongly suggested that the clones might encode a μ-conotoxin. Despite the significant sequence divergence from previously characterized μ-conotoxins (μ-GIIIA, 82 -GIIIB and μ-GIIIC from *Conus geographus*) there were a number of important features similar to these earlier characterized conotoxins. These similarities include: the pattern of Cys residues, the high net positive charge, and the apparent conservation of the critical Arg residue (residue 14 of the predicted mature peptide) believed to be essential for μ-conotoxin function (Sato et at., 1991; Becker et at., 1992).

Example 2 Synthesis of μ-Conotoxin Peptide PIIIA Sequence

The predicted 22-residue peptide, including post-translational modifications modeled on other related peptides was chemically synthesized. The post-translational modifications include changing Gln1 to pyroglutamate, prolines to hydroxyproline, the C-terminal Cys-Cys-Gly-Arg (SEQ ID NO: 2) to Cys—Cys—$NH_2$. The resulting peptide, with the disulfide bonding indicated, is referred to as μ-conotoxin PIIIA (μ-GIIIA) based on the physiological evidence detailed below. The structure is:

```
    |     |   |   |
ZRLCCGFOKSCRSRQCKOHRCC—NH2    SEQ ID NO:1
    |         |
``` where Z=pyroglutamate and O=4-trans-hydroxyproline. The pure synthetic peptide caused flaccid paralysis in both mice and fish, as expected for μ-conotoxin.

The peptide was built in two stages based on the linear sequence predicted from the cDNA isolate. First, the protected peptide resin minus the N-terminal pyroglutamate was built by standard Fmoc chemistry on an ABI model 477A peptide synthesizer. Pyroglutamate was then added manually to some of the resin to produce the complete peptide. After cleavage from the respective resins, the linear peptides ([1-22] and [-22]) were purified by preparative reversed phase HPLC. Disulfide bridges were allowed to form in the presence of a glutathione redox buffer, and the products were again fractionated by preparative HPLC. The major oxidation products in each case were obtained in highly purified form.

Peptide bond coupling was carried out with equimolar amounts of amino acid derivative, DCC and HOBT, and the terminal Fmoc group was removed by treatment with piperidine/NMP (20% by volume). The side chain Fmoc-protected amino acids were purchased from Bachem (Torrance, CA); these are Hyp (t-Bu), Lys (Boc), Ser (t-Bu), Arg (pmc), Gln (trt), His (trt) and Cys (trt). In the second stage, pyroglutamic acid was manually coupled to the peptide resin. Pyroglutamic acid (0.25 mmol; Sigma) was activated in 1 ml solution of 1 M DICC/1 M HOBT in NMP for 30 minutes, and the solution was added to 100 mg (0.012 mmol) peptide resin. The reaction mixture was stirred for 2.5 hours and centrifuged. The resin was then washed with NMP five times, followed by three washes with methanol. Because the pyroglutamate was not protected, the removal of an Fmoc group was not necessary. The final resin was dried, and subjected to peptide cleavage as described previously (Shon et at., 1995). The cleavage mixture was filtered into tert-butyl methyl ether at −10° C. Peptides immediately precipitated, and the solution was centrifuged to separate the pellet, which was washed three times with the ether.

The pellet was dissolved in 60% acetonitrile containing 0.1% TFA, and purified by reversed phase HPLC. Several runs were required on both preparative and semi-preparative columns to obtain pure linear peptide. The glutathione oxidation protocol previously described (Hopkins et ai., 1995) was used to oxidize the linear peptide. The major peak from overnight oxidation was repurified on both preparative and semi-preparative columns.

To obtain the unblocked analog μ-PIIIA[2-22], the same cleavage and oxidation procedures were carried through on a sample of resin before the pyroglutamate was added.

Example 3 Iodination of μ-Conotoxin PIIIA[2-22]

The peptide solution (5–10 nmol) in sodium phosphate buffer (0.25 M, pH 7.5) (about 0.4 ml) was incubated with an equal volume of 2 mM $I_2$ dissolved in methanol, for 10 minutes at ambient temperature. The reaction mixture was quenched with ascorbic acid, and then subjected to reversed phase HPLC. With this incubation time, most of the product was the di-iodinated peptide. Shorter incubations were used to prepare the mono-iodinated derivative.

Example 4 Disulfide Bridge Analysis

Disulfide bridge analysis was carried out on two analogs (the peptide without an N-terminal pyroglutamate, and the same peptide with the His residue di-iodinated). The disulfide connectivity of μ-PIIIA[2-22] was analyzed by the partial reduction strategy of Gray (Gray, 1993), and found to be the same as that of the known μ-conotoxins from *C. geographus*. The shorter analog was chosen for analysis, because the terminal pyroglutamate of the full-length peptide greatly complicates sequencing. Partial reduction with TCEP gave intermediates that were not well resolved from fully reduced or fully oxidized peptides, and only one suitable product could be isolated. This was labeled with iodoacetamide, then reduced and further labeled with 4-vinylpyridine; the pattern of labeling showed that it represented an intermediate with a single disulfide between Cys3 (residue 11 ) and Cys6 (residue 22).

The analysis was completed using the monoiodohistidine derivative of μ-PIIIA[2-22], which gave three intermediates that were shifted away from the fully reduced and fully oxidized peptides. One of these proved to have a single disulfide between Cys2 (residue 4) and Cys5 (residue 21); a second had been reduced only at the Cys3–Cys6 bridge; the third, though not sequenced completely, appeared to be analogous to the product obtained form the non-iodinated peptide. Thus, all results are consistent with a disulfide connectivity exactly equivalent to that of the μ-GIII series of toxins (Cys1–Cys4; Cys2–Cys5; Cys3–Cys6). The sequences and disulfide connectivity of all known μ-conotoxins are shown in Table I.

sheet into each slot. To prevent the Mylar partitions from cutting into the muscle pinned to the floor of the trough, two strips of Mylar (~1 mm wide×15 mm long×0.1 mm thick) were placed on either side of the muscle to serve as stops. All four compartments contained Ringer's solution. Stimulating electrodes were located in the first two compartments (A and B), and recording electrodes were located in the second two compartments (C and D). A ground electrode was located in compartment B. All electrodes were bare Pt wires. The recording electrode in C was connected to the negative input, and that in D to the positive input, of a differential AC preamplifier. The stimulating electrodes were connected to a stimulus isolation unit, and supramaximal, 1 ms-long rectangular pulses were used to directly elicit action potentials in the muscle. Stimuli were applied at a frequency of 1/minute or less. When the action potential propagated into chamber C, a positive response was recorded by the S preamplifier, and the further propagation of the action potential into chamber D was registered by the preamplifier as a negative response. Thus, the extracellularly recorded action potential from the population of fibers in the muscle was recorded as a biphasic response, with the phases separated from each other by only a few milliseconds (see FIG. 4B). To examine the effect of the toxin, the plain Ringer's solution in chamber D was replaced by one containing toxin. If the toxin blocked sodium channels, attenuation of only the late negative phase should

TABLE I

Comparison of Sequences of Known μ-Conotoxins

μ-PIIIA    ZRLCCGFOKSCRSRQCKOHRCC*    SEQ ID NO: 1

μ-GIIIA    RDCCTOOKKCKDRQCKOQRCCA*    SEQ ID NO: 3
μ-GIIIB    RDCCTOORKCKDRRCKOMKCCA*    SEQ ID NO: 4
μ-GIIIC    RDCCTOOKKCKDRRCKOLKCCA*    SEQ ID NO: 5

Disulfide Bonding: CC---C---C---CC

Z = pyroglutamate; O = 4-trans-hydroxyproline

Arrow indicates the conserved Arg.

*indicates an amidated carboxy terminus; the amidation for GIIIC was not directly determined experimentally, but is inferred by homology.

Example 5 Electrophysiology

Figure 2A:
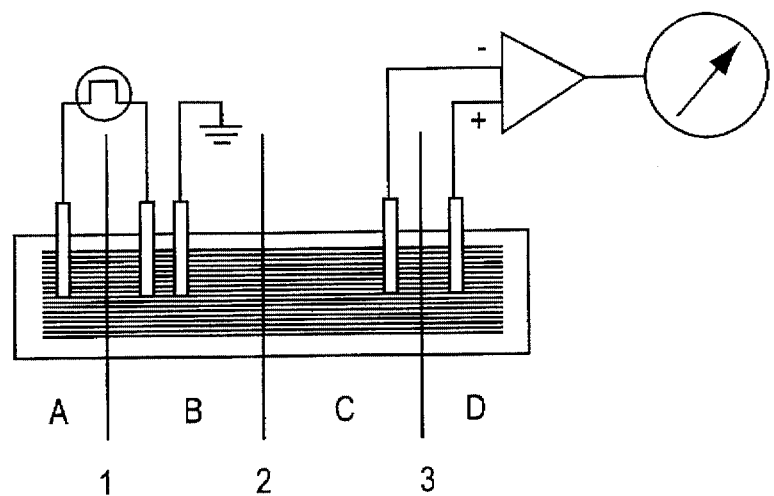
FIG. 2A is a sketch of electrophysiological recording chamber for testing toxin on frog cutaneus pectoris muscle's response to direct electrical stimulation. A rectangular Sylgard trough was partitioned into four compartments (A through D) by three Mylar sheets (1-3). Mylar sheets were inserted into slots in the wall of the trough after the muscle had been pinned to the floor of the trough. The cutaneus end of the muscle was in A and the episternum (cartilage) was in D. Stimulating electrodes were in A and B (i.e., stimulation was across partition 1). A ground electrode was in B. Recording electrodes were in C and D (with electrode in D leading to the "+" input of the preamp). Compartment D served as the test chamber—only it was exposed to toxin.

The effects of the peptide on frog muscle (cutaneus pectoralis) were investigated. A sketch of the recording chamber is shown in FIG. 2A. Current was injected into the muscle across partition 1; the recording electrodes monitored the potential across partition 3. Partition 2 served to electrically isolate the recording from the stimulating electrodes. Toxin was added only into the compartment D.

The cutaneus pectoris muscle from ~7 cm *Rana pipiens* frogs was used. The muscle was trimmed longitudinally so that only the lateral one-quarter of muscle remained (cf. Yoshikami et at., 1989). The trimmed muscle was pinned flat on the floor of a shallow trough (~4 mm×16 mm—1 mm deep) fabricated from Sylgard (a silicone elastomer, Dow Chemical Co.). The trough had four transverse slits cut into its wall by a razor blade (see FIG. 4A). Thus, once the muscle was pinned in place, the trough could be partitioned into four compartments by inserting a 0.1 mm thick Mylar be observed. The early positive phase should remain largely unaltered reflecting the fact that portions of the muscle not exposed to toxin remained normal. Thus, there are two advantages of exposing only the solution in chamber D to toxin. One, this allows the response in chamber C to serve as an internal control for the overall vitality of the muscle preparation as well as to insure that the stimulus remained supramaximal; and two, the volume of toxin solution necessary is reduced, in these experiments 25 μl sufficed.

Figure 2B:
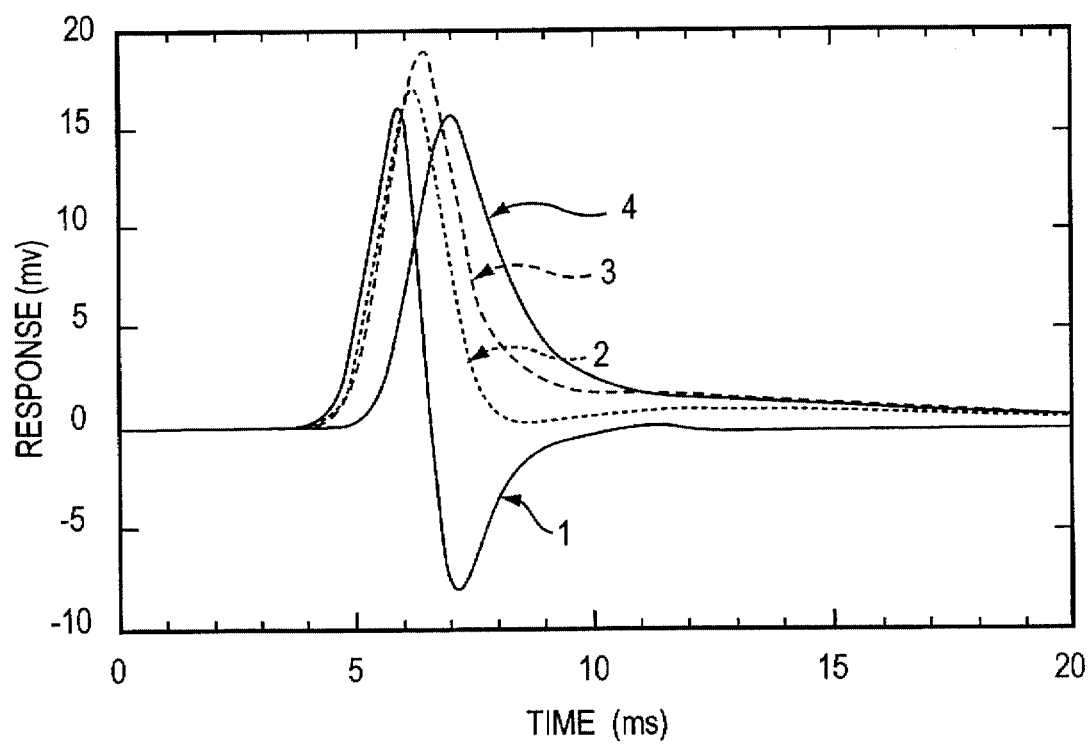
FIG. 2B shows that PIIIA at a concentration of 1 μM blocks directly-evoked action potentials in frog muscle. Superimposed traces of responses before, during and after exposure to toxin are shown. The stimulus was applied at t=0. Curve 1 is for a control sample response. Curve 2 shows a response after exposure to toxin for 23 minutes and just before the toxin was washed out. Curve 3 shows the response 20 minutes after toxin washout. Curve 4 shows the response after >4.5 hours of washing. Toxin was placed only in one compartment (D in FIG. 2A), and it contained the portion of the muscle which produced the negative phase of the response in the control trace.
Figure 2C:
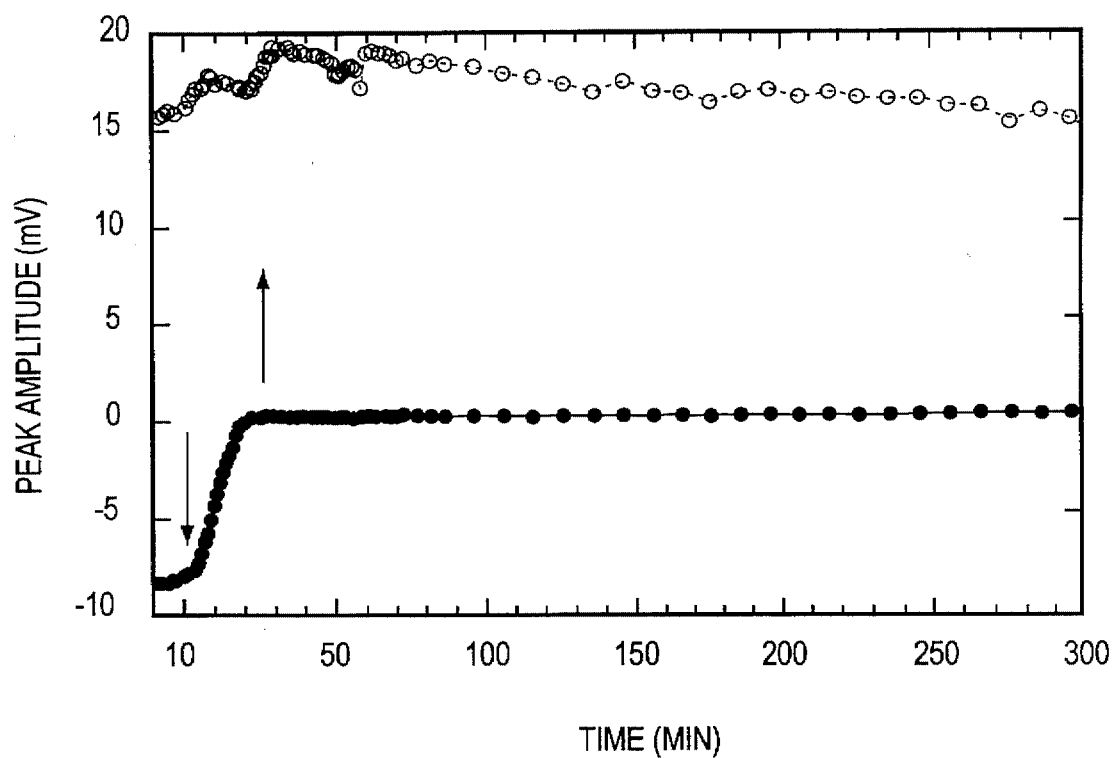
FIG. 2C shows the time course of block of directly-evoked action potentials. Maximum amplitudes of the positive phase (open circles) and negative phase (closed circles) of the response are plotted as a function of time. Solution in compartment D was replaced with 1 μM PIIIA at time 0 (downward arrow), and the toxin was washed out 23 minutes later (upward arrow).

A control response before toxin addition is shown in FIG. 2B. The progression of the action potential between segments C and D is readily apparent; the biphasic waveform generated represents propagation of the action potential from C to D. The peaks of the responses as a function of time before, during, and after toxin addition are shown in FIG. 2C. With the toxin added to segment D, the action potential clearly propagated into segment C, causing the voltage change characteristic of the first half of the biphasic waveform in FIG. 2B; however, the negative phase was completely abolished, indicating that although a normal action potential was generated, transmission in segment D of the muscle was abolished. These results are consistent with inhibition of voltage-gated sodium channels on the muscle plasma membrane. Even upon washing for many hours in the absence of toxin, no recovery was observed in segment D (see FIG. 2C), although action potential propagation to segment C was essentially normal (a slight rundown was observed with time). Similar results were also observed with the μPIIIA[2-22] analog of the toxin (results not shown). During exposure to toxin, the amplitude of the positive phase increased somewhat while that of the negative phase was abolished as is also evident in FIG. 2A. Upon washout of toxin, the amplitude of the negative phase remained nil while that of the positive phase continue to increase slightly for about 10 minutes before slowly and continuously decreasing over the next 4 hours. This decline continued at essentially a constant rate for the next 13 hours (not shown) at which time the response was ~10 mV, and the experiment was terminated. These experiments show that the negative phase is completely, and irreversibly obliterated by exposure to toxin, whereas the positive phase remains largely intact indicating that no untoward systemic changes occurred. Upon exposure to toxin, the positive phase initially becomes larger because the counteracting negative phase becomes smaller. The initial rising phase of the positive phase is also slightly delayed following exposure to toxin; this is thought to be due to leakage of the toxin into compartment C with an attendant decrease in the propagation velocity of the action potential in that compartment. Leak of toxin into compartment C is also thought to be responsible for the decrement in the amplitude of the positive phase as well as delayed time to peak observed in the response taken >4.5 hours later.

Nerve-muscle preparations were also examined; when the motor nerve was electrically stimulated, a muscle action potential was recorded and a muscle twitch observed. When the entire nerve-muscle preparation was exposed to toxin, muscle twitching and action potentials were completely abolished; however, excitatory post-synaptic responses were still recorded (results not shown). Thus, propagation of action potentials in the motor axon is not blocked, unlike action potential propagation in muscle.

The results are consistent with the activity of a μ-conotoxin; the homologous peptides from *Conus geographus* have previously been shown to be highly specific for the skeletal muscle Na$^+$ channel subtype in peripheral systems. Although μ-GIIIA and μ-PIIIA selectively inhibit skeletal muscle action potentials, a notable difference is that the latter peptide appears to act much more irreversibly in the frog neuromuscular preparation. The new peptide should be the most convenient pharmacological agent available for irreversibly preventing muscle twitching when the synaptic electrophysiology of amphibian neuromuscular junctions is investigated.

Example 6 Binding Competition Experiments

In order to further establish that the peptide is a μ-conotoxin, binding displacement experiments were performed with [$^3$H]saxitoxin as the radiolabeled ligand, and *Electrophorus electricus* electric organ membranes as the source of receptors (FIG. 3). [$^3$H]Saxitoxin binding to rat brain membranes was carried out by the protocol of Doyle et al. (1993) except that the assays were scaled down to a volume of 0.25 ml and 1 mM PMSF, 1 μM leupeptin and 1 μM pepstatin were present. Electric eel membranes were prepared as described by Becker et al. (1989) except that the homogenizing buffer used was 10 mM HEPES-Tris, 10 mM EDTA, 10 mM EGTA, 1 mM PMSF, 1 μM leupeptin and pepstatin, pH 7.0.

As expected, μ-conotoxin PIIIA displaces [$^3$H]saxitoxin binding to electric organ membranes, which contain a high density of the skeletal muscle subtype of voltage-gated sodium channels. Clearly, μ-conotoxin PIIIA has a high affinity ($K_D$~$3\times10^{-9}$M) for the saxitoxin binding site in the electric organ.

Figure 3:
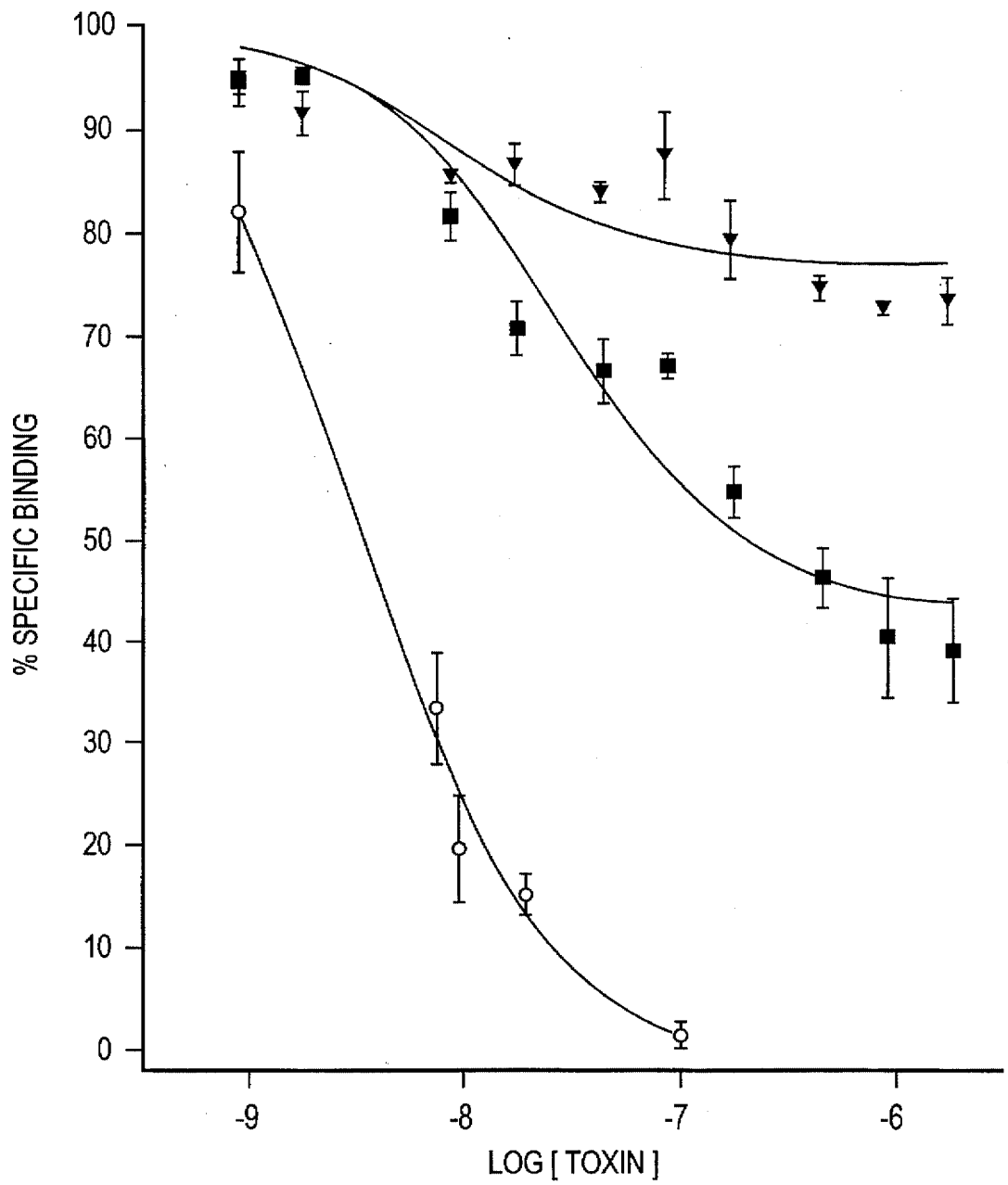
FIG. 3 shows the results of binding competition experiments with [$^3$H]saxitoxin (SXT). Specific binding was determined by subtracting nonspecific binding of [$^3$H]saxitoxin from total binding; the nonspecific binding was measured by using 12 μM tetrodotoxin (TTX) to displace [$^3$H]saxitoxin binding. Open circles, μ-PIIIA displacement for eel electroplax sites; squares, μ-PIIIA displacement for rat brain sites; triangles, μ-GIIIA displacement for rat brain sites

Somewhat surprisingly, it was found that μ-PIIIA also displaced a significant fraction (>50%) of specific [$^3$H] saxitoxin binding to crude membranes from rat brain. A comparison of μ-PIIIA and μ-GIIIA displacement of specific [$^3$H]saxitoxin binding to rat brain sites is shown in FIG. 3. These data indicate that μ-PIIIA displaces more than half of the [$^3$H]saxitoxin high affinity sites in rat brain (apparent $K_D$~30 nM); in contrast, μ-GIIIA displaced about 20% of specific [$^3$H]saxitoxin binding at the same concentrations. These results suggest that there are μ-GIIIA-sensitive, μ-GIIIA-resistant Na$^+$ channels in the mammalian CNS.

Example 7 Central Nervous System (CNS) Electrophysiology

In order to establish directly whether μ-conotoxin PIIIA could affect voltage-gated sodium channels in the CNS, the effect of the toxin was tested on a major subtype of voltage-gated sodium channels found in central neurons, the Type II voltage-gated sodium channels (FIG. 4). Oocytes from *Xenopus laevis* were prepared as described previously (St ühmer, 1992). mRNA encoding rat Type II sodium channel α-subunit (Noda et at., 1986) was injected into stage VI oocytes (30–50 ng/oocyte). The vitelline membranes of the oocytes were removed mechanically with fine forceps and currents were recorded 2–6 days after injection under two-electrode voltage clamp control with a Turbo-Tec amplifier (NPI Elekronik, Tamm, Germany) driven by the Pulse+ PulseFit software package (HEKA Electronik, Lambrecht, Germany). Intracellular electrodes were filled with 2 M KCl and had a resistance between 0.6 and 0.8 MΩ. Current records were low-pass filtered at 3 kHz and sampled at 10 kHz. The bath solution was normal frogs Ringer's (NFR) containing (in mM): 115 NaCl, 2.5 KCl, 1.8 CaCl$_2$, 10 Hepes pH 7.2 (NaOH). Leak and capacitive currents were corrected on-line by using a P/n method. Toxin solution was prepared in NFR added to the bath chamber.

Figure 4C:
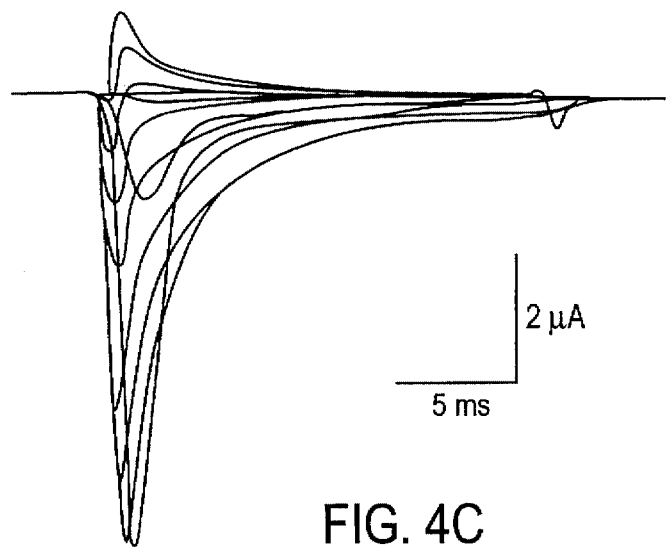

The Type II voltage-gated sodium channels were previously shown to be TTX-sensitive but resistant to 1–2 μM of μ-conotoxin GIIIA (Terlau et at., 1996; Noda et at., 1986). μ-PIIIA blocked type II Na$^+$ channels from rat expressed in Xenopus oocytes (Noda et at., 1986); the presence of μ-PIIIA (2 μM) in the bath solution abolished nearly all Na$^+$ currents (FIG. 4B), but in a reversible manner (FIG. 4C). Thus, rat brain Type II Na$^+$ channels apparently belong to the TTX- and μ-GIIIA-sensitive, but μ-GIIIA resistant class of Na$^+$ channels in the mammalian CNS.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Becker, S. et at. (1989). Synthesis and characterization of μ-conotoxin IIIA. *Eur. J. Biochem.* 185:79–84.

Becker, S. et al. (1992). Action of derivatives of μ-conotoxin GIIIA on sodium channels. Single amino acid substitutions in the toxin separately affect association and dissociation rates. *Biochemistry* 31:8229–8238.

Bodansky et at. (1966). *Chem. Ind* 38:1597–98.

Carterall, W. A. (1992). Cellular and molecular biology of voltage-gated sodium channels. *Physiol. Rev. Supp.* 72:S15–48.

Colledge, C. J. et al. (1992). Precursor structure of ω-conotoxin GVIA determined from a cDNA clone. *Toxicon* 30:1111–1116.

Cruz, L. J. et at. (1985). Conus geographus toxins that discriminate between neuronal and muscle sodium channels. *J. Bid. Chem.* 260:9280–9288.

Doyle, D. D. et al. (1993). Divalent cation competition with [$^3$H]saxitoxin binding to tetrodotoxin-resistant and -sensitive sodium channels. *J. Gen. Physiol.* 101:153–182.

Dudley, S. C. et at. (1995). A μ-Conotoxin-Insensitive Na$^+$ Channel Mutant: Possible Localization of a Binding Site at the Outer Vestibule. *Biophys. J.* 69:1657–1665.

Gray, W. R. (1993). Disulfide Structures of Highly Bridged Peptides: A New Strategy for Analysis. *Protein Science* 2:1732–1748.

Hillyard, D. R. et al. (1992). A new Conus peptide ligand for mammalian presynaptic Ca$^{2+}$channels. *Neuron* 9:69–77.

Hopkins, C. et al. (1995). A new family of Conus peptides targeted to the nicotinic acetylcholine receptor. *J. Biol. Chem.* 270:22361–22367.

Horiki, K. et al. (1978). *Chemistry Letters* 165–68.

Kaiser et at. (1970). *Anal. Biochem.* 34:595.

Kapoor (1970). *J. Pharm. Sci.* 59:1–27.

Kornreich, W. D. et al. (1986). U.S. Pat. No. 4,569,967.

*Methoden der Organischen Chemie (Houben-Weyl): Synthese von Peptiden*, E. Wunsch (Ed.), Georg Thieme Verlag, Stuttgart, Ger. (1974).

Miljanich, G. P. et al. (1993). U.S. Pat. No. 5,264,371.

Myers, R. A. et at. (1993). Conus Peptides as Chemical Probes for Receptors and Ion Channels. *Chem. Rev.* 93:1923–1936.

Narahashi, T. et at. (1964). Tetrodotoxin blockage of sodium conductance increase in lobster giant neurons. *J. Gen. Physiol.* 47:965–974.

Noda, M. et at. (1986). Existence of distinct sodium channel messenger RNAs in rat brain. *Nature* 320:188–191.

Olivera, B. M. et al. (1984). U.S. Pat. 4,447,356.

Olivera, B. M. et at. (1985). Peptide neurotoxins from fish-hunting cone snails. *Science* 230: 1338–1343.

Olivera, B. M. et at. (1990). Diversity of Conus neuropeptides. *Science* 249:257–263.

Olivera, B. M. et al. (1994). Calcium channel diversity and neurotransmitter release: The ω-conotoxins and ω-agatoxins. *Ann. Rev. Biochem.* 63:823–867.

Rivier, J. R. et al. (1978). *Biopolymers* 17:1927–38.

Sambrook, J. et at. (1979). *Molecular Cloning: A Laboratory Manual*, 2nd Ed., Cold Spring Harbor Laboratory, Cold Spring Harbor, N.Y.

Sato, S. et at. (1983). The amino acid sequences of homologous hydroxyproline containing myotoxins from the marine snail Conus geographus venom. *FEBS Lett.* 155:277–280.

Sato, K. et at. (1991). Active site μ-conotoxin GIIIA, a peptide blocker of muscle sodium channels. *J. Biol. Chem.* 266:16989–16991.

Schroder & Lubke (1965). *The Peptides* 1:72–75, Academic Press, N.Y.

Shon, K. et al. (1995). Purification, characterization and cloning of the lockjaw peptide from Conus purpurascens venom. *Biochemistry* 34:4913–4918.

Stewart and Young, *Solid-Phase Peptide Synthesis*, Freeman & Co., San Francisco, Calif. (1969).

Stone, B. L. and Gray, W.R.. (1982). Occurrence of hydroxyproline in a toxin from the marine snail Conus geographus. *Arch. Blochem. Biophys.* 216:756–767.

Stühmer, W. (1992). Electrophysiological recordings from Xenopus oocytes. *Meth. Enzymol.* 207:319–339.

Terlau, H. et al. (1996). μO-Conotoxin MrVIA inhibits mammalian sodium channels but not through Site I. *J. Neurophysiol.*, submitted.

Vale et al. (1978). U.S. Pat. 4,105,603.

Woodward, S. R. et al. (1990). Constant and hypervariable regions in conotoxin propeptides. *EMBO J.* 1:1015–1020.

Yoshikami, D. et al. (1989). The inhibitory effects of omega-conotoxins on calcium channels and synapses. *Ann. N.Y. Acad. Sci.* 560:230–248.

U.S. Pat. 3,972,859 (1976).

U.S. Pat. 3,842,067 (1974).

U.S. Pat. 3,862,925 (1975).

---

What is claimed is:

1. An isolated, or purified μ-conotoxin consisting of the amino acid sequence Xaa$_1$-Arg-Leu-Cys-Cys-Gly-Phe-Xaa$_2$-Lys-Ser-Cys-Arg-Ser-Arg-Gln-Cys-Lys-Xaa$_2$-His-Arg-Cys-Cys (SEQ ID NO: 1) where Xaa$_1$ is pyroglutamate or glutamine and Xaa$_2$ is 4-trans-hydroxyproline or proline.

2. The peptide of claim 1 wherein the carboxy terminus is amidated.

3. An isolated, or purified peptide consisting of the amino acid sequence Glu-Lys-Arg-Gln-Arg-Leu-Cys-Cys-Gly-Phe-Pro-Lys-Ser-Cys-Arg-Ser-Arg-Gln-Cys-Lys-Pro-His-Arg-Cys-Cys-Gly-Arg (SEQ ID NO:7).

4. The μ-conotoxin of claim 1 wherein said μ-conotoxin is obtained by chemical synthesis.

5. The μ-conotoxin of claim 4 wherein the carboxy terminus is amidated.

6. The peptide of claim 3 wherein said peptide is obtained by chemical synthesis.

* * * * *